United States Patent
Kruecker et al.

(10) Patent No.: US 9,814,442 B2
(45) Date of Patent: Nov. 14, 2017

(54) SYSTEM AND METHOD FOR NEEDLE DEPLOYMENT DETECTION IN IMAGE-GUIDED BIOPSY

(75) Inventors: Jochen Kruecker, Washington, DC (US); Pingkun Yan, Xi'an (CN); Alper Ayvaci, Los Angeles, CA (US)

(73) Assignee: Koninklijke Philips N.V., Eindhoven (NL)

( * ) Notice: Subject to any disclaimer, the term of this patent is extended or adjusted under 35 U.S.C. 154(b) by 232 days.

(21) Appl. No.: 13/978,552

(22) PCT Filed: Jan. 12, 2012

(86) PCT No.: PCT/IB2012/050158
§ 371 (c)(1),
(2), (4) Date: Jul. 8, 2013

(87) PCT Pub. No.: WO2012/098483
PCT Pub. Date: Jul. 26, 2012

(65) Prior Publication Data
US 2013/0289393 A1    Oct. 31, 2013

Related U.S. Application Data

(60) Provisional application No. 61/433,284, filed on Jan. 17, 2011.

(51) Int. Cl.
*A61B 8/00* (2006.01)
*A61B 8/08* (2006.01)
(Continued)

(52) U.S. Cl.
CPC .......... *A61B 8/0841* (2013.01); *A61B 8/4245* (2013.01); *A61B 8/4254* (2013.01); *A61B 10/0275* (2013.01); *A61B 34/20* (2016.02); *A61B 10/0241* (2013.01); *A61B 2034/2051* (2016.02); *A61B 2090/365* (2016.02); *A61B 2090/378* (2016.02)

(58) Field of Classification Search
CPC ... A61B 8/0833; A61B 8/0841; A61B 8/4245; A61B 8/4416; A61B 19/52; A61B 2019/5291; A61B 10/0241; A61B 19/5244
See application file for complete search history.

(56) References Cited

U.S. PATENT DOCUMENTS 5,957,844 A    9/1999  Dekel et al.
6,246,898 B1 *  6/2001  Vesely et al. ................. 600/424
(Continued)

FOREIGN PATENT DOCUMENTS

CN    101132744 A    2/2008
EP    1864624        12/2007
(Continued)

*Primary Examiner* — Joel Lamprecht (57) ABSTRACT

A system and method for medical device detection includes a guidance system (38) configured to deliver a surgical device (32) into a subject. A surgical device deployment detector (25, 40, 42, 44) is configured to cooperate with the guidance system and is configured to detect a deployment of the surgical device in the subject. A coordination module (22) is configured to receive input from the guidance system and the deployment detector to determine and record one or more of a location and time of each deployment.

21 Claims, 7 Drawing Sheets

(51) Int. Cl.
   *A61B 34/20* (2016.01)
   *A61B 10/02* (2006.01)
   *A61B 90/00* (2016.01)

(56) References Cited

U.S. PATENT DOCUMENTS

| | | |
|---|---|---|
| 6,336,899 B1 | 1/2002 | Yamazaki |
| 6,546,279 B1 * | 4/2003 | Bova et al. .................. 600/437 |
| 6,764,449 B2 | 7/2004 | Lee et al. |
| 2002/0156376 A1 | 10/2002 | Wang et al. |
| 2003/0135115 A1 * | 7/2003 | Burdette et al. ............. 600/437 |
| 2005/0182316 A1 | 8/2005 | Burdette et al. |
| 2007/0238981 A1 | 10/2007 | Zhu et al. |
| 2009/0154293 A1 | 6/2009 | Sengupta et al. |
| 2009/0247876 A1 | 10/2009 | Cannon, Jr. et al. |
| 2010/0172559 A1 | 7/2010 | Kumar et al. |
| 2010/0268085 A1 | 10/2010 | Kruecker et al. |
| 2010/0298704 A1 | 11/2010 | Pelissier et al. |
| 2013/0289393 A1 | 10/2013 | Kruecker et al. |

FOREIGN PATENT DOCUMENTS

| | | |
|---|---|---|
| JP | S5581640 A | 6/1980 |
| JP | H09271472 A | 10/1997 |
| JP | 2005087591 A | 4/2005 |
| JP | 2005342128 A | 12/2005 |
| JP | 2007195867 A | 8/2007 |
| WO | WO2004019799 | 3/2004 |

* cited by examiner

SYSTEM AND METHOD FOR NEEDLE DEPLOYMENT DETECTION IN IMAGE-GUIDED BIOPSY

This disclosure relates to surgical procedure imaging, and more particularly to a system and method for detecting surgical instruments during biopsy procedures.

Prostate cancer is currently the second leading cause of cancer death in American men. In many situations, patients are being diagnosed for prostate cancer using a "blind" transrectal ultrasound (TRUS)-guided systematic biopsy. Ultrasound imaging, however, merely guides the needle to different regions of the prostate, and may not visualize prostate cancer reliably. Multi-parametric magnetic resonance imaging (MRI) has good sensitivity and specificity in detecting prostate cancer. Efforts have been made to create image guidance applications that can fuse real-time TRUS with pre-acquired MRI to guide needles to diagnostic or therapeutic target sites identified in MRI.

In MRI/TRUS fusion guided targeted prostate biopsy and therapy, there are several situations in which it is important to know an exact location of the deployment of the biopsy needle. For example, biopsy needle tip localization plays a role in retrospective analysis of the image fusion system. In prostate biopsy, the biopsy needle is deployed by using a biopsy gun. The needle tip for tissue sampling may not exactly hit the planned target site. For repeat biopsies, physicians may want to re-sample regions with suspicious findings in earlier biopsies, or may want to specifically avoid re-sampling regions with benign findings and target areas in between previous biopsies instead. In both cases, the exact locations of earlier biopsy samples need to be known. Furthermore, locations of the positive biopsies are needed in addition to imaging findings for planning focal therapy.

In accordance with the present principles, a system and method for medical device detection includes a guidance system configured to deliver a surgical device into a subject. A surgical device deployment detector is configured to cooperate with the guidance system and configured to detect a deployment of the surgical device in the subject. A coordination module is configured to receive input from the guidance system and the deployment detector to determine and record one or more of a location and time of each deployment.

A biopsy system for medical device detection includes a guidance system configured to deliver a biopsy needle into a subject, a deployment detector configured to detect deployment of the biopsy needle and a scanning probe employed to image the biopsy needle, and an imaging device configured to image the deployment. A coordination module is configured to receive input from one or more of the guidance system, the deployment detector and the scanning probe to record each deployment to create a record of location and time of a biopsy associated with each deployment.

A method for medical device detection includes delivering a surgical device into a subject using a guidance system; integrating surgical device guidance with automatic deployment detection and recordation to detect an occurrence of a deployment of the surgical device with one or more of a real-time image, an acoustic indicator, a vibration detector and a spatial tracking device; and determining and recording one or more of a location and time of each deployment based upon the surgical device guidance and automatic deployment detection.

In one embodiment, actual biopsy locations in a procedure are found and then the actual biopsy locations are mapped to magnetic resonance (MR) images. The targets identified on a multi-parametric MR can then be correctly correlated with the pathological analysis results.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, systems and methods for detecting surgical instrument deployment during surgical procedures are disclosed. In one embodiment, the surgical instrument may include a biopsy needle. The surgical procedures may be integrated into an image-guided navigation system for tracking biopsy locations. The systems and methods track a number, time, and location of biopsies using the navigation system. In one embodiment, needle deployment position is automatically recorded during image-guided biopsy procedures, e.g., a firing time and needle location can be automatically recorded for a biopsy gun fired during a biopsy procedure. Methods for detecting needle deployment based on images, sound, and motion are provided. The detection system can be incorporated into an image-guided biopsy navigation system as an additional feature.

It also should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 1:
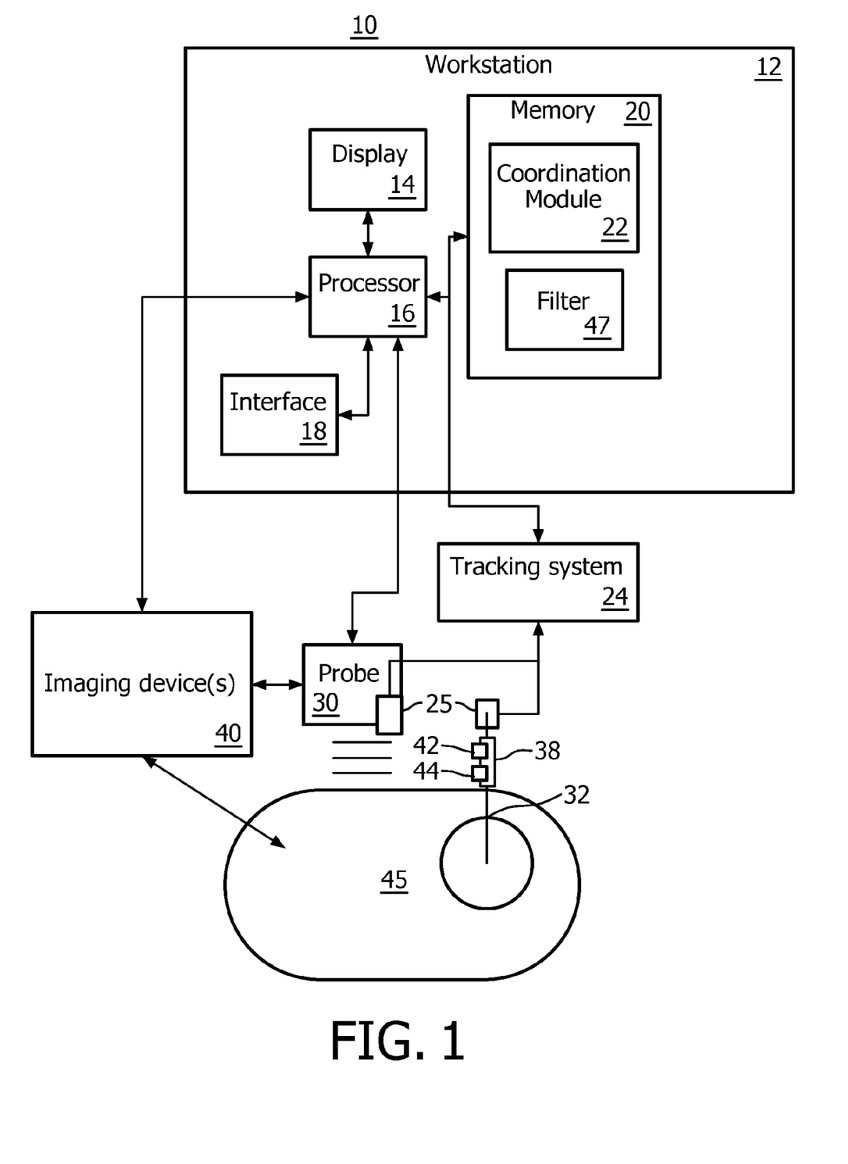
FIG. 1 is a block/flow diagram showing a system/method with integrated surgical instrument guidance and deployment detection in accordance with the present principles.

Referring now to the drawings in which like numerals represent the same or similar elements and initially to FIG. 1, a system 10 for integrating needle guidance for biopsies with automatic needle deployment detection and recording is illustratively shown in accordance with one embodiment. System 10 may be applied in a variety of clinical procedures, e.g., in image-guided biopsies. In particular, the system 10 may assist in automatically documenting a number, time, and location of biopsies performed under image-guided navigation systems on a patient 45. System 10 includes a workstation 12 that provides planning, navigation and feedback information to a user using, e.g., a display 14. The workstation 12 may include a computer processor 16, the display 14, a user interface 18 (e.g., mouse, keyboard, etc.) and memory 20 for storing data and software.

Memory 20 includes software, which may include a coordination module 22 configured to coordinate image information, acoustic or vibratory information, spatial tracking data, etc. with medical instrument motion and events associated with the treatment of a subject. In one embodiment, a position of an ultrasonic probe 30 and a biopsy needle 32 are concurrently tracked. Biopsy positions are determined using image guidance and recorded with reference to a medical image or images. In another embodiment, a spatial tracking system 24 and tracking device 25 may be employed to determine a probe position relative to a medical image. For example, a 6 degree-of-freedom electromagnetic (EM) tracking sensor can be placed on the probe 30 as the tracking device 25. The module 22 collects data indicating a position of a deployment guidance system 38 (such as a needle guide, biopsy gun or other device), a needle 32, or any other instrument.

The deployment guidance system 38 is instrumented to provide deployment detection of instrument 32 motion and/or triggering (e.g., collection of a sample). Module 22 coordinates the integration of automatic instrument deployment detection, position determination and recording using the instrumented tools and systems in accordance with the present principles. The detection may be from images, e.g., transrectal ultrasound images/video stream, collected from an imaging device 40. In one embodiment, a filter 47 is employed to assist in tracking the instrument 32 with an image of the subject 45. In other embodiments, the detection may be from an acoustic detector 42, or from a vibration detector 44 and/or from spatial tracking data from tracking device 25, e.g., from a tracked biopsy needle and/or probe 30. Using one or more of these devices, at least the time and location of events (biopsy sample) can be determined within a subject. The detection of deployment operations of instrument 32 may be correlated with a reference coordinate system so that time and location of, e.g., biopsy sample, may be recorded for future reference.

In one embodiment, it would be very useful to find actual biopsy locations in a procedure and then map the actual biopsy locations to a reference image, e.g., magnetic resonance (MR) images. The targets identified on a multi-parametric MR can then be correctly correlated with the pathological analysis results.

Figure 2:
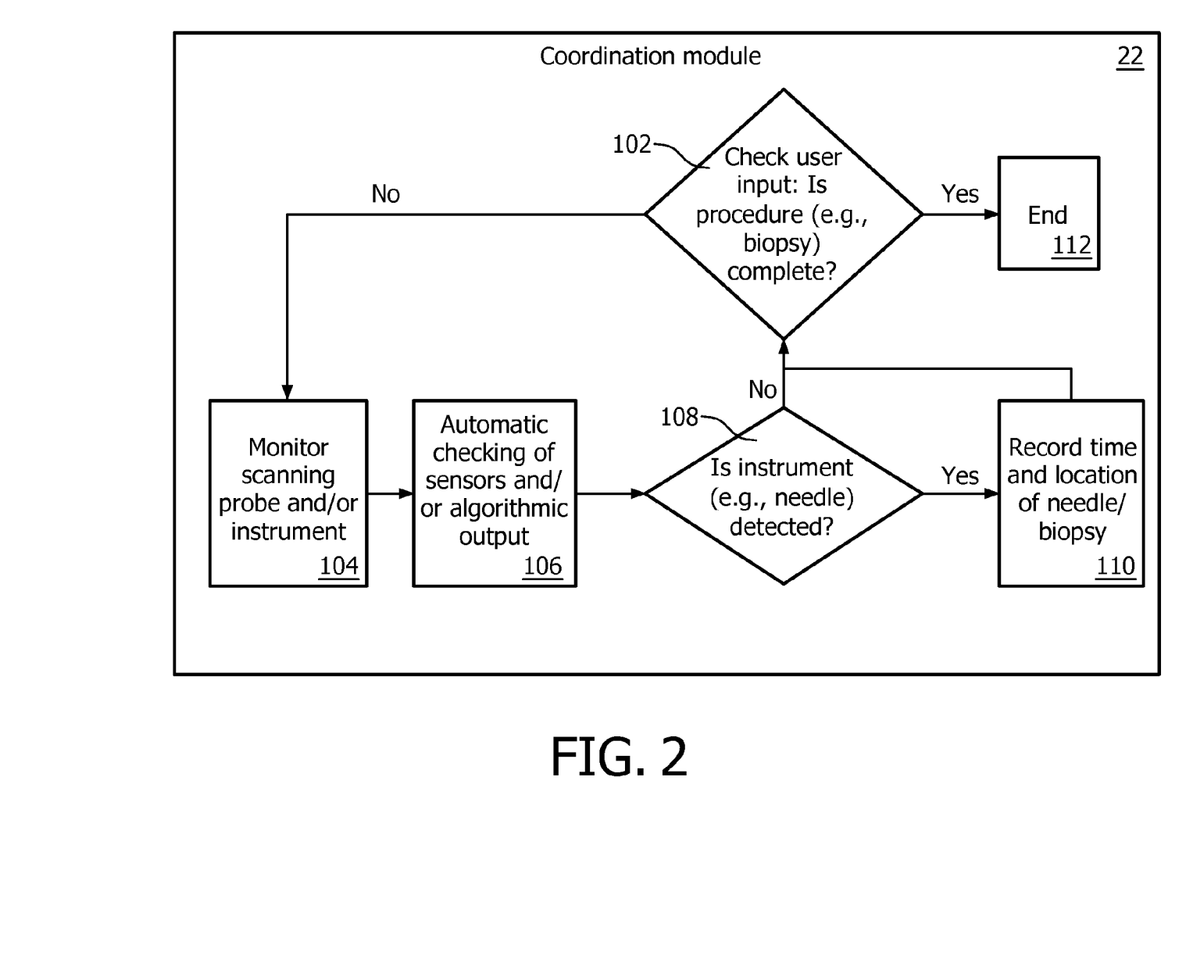
FIG. 2 is a block/flow diagram showing a system/method for a workflow of a coordination module for an image-guided biopsy in accordance with the present principles.

Referring to FIG. 2, a block/flow diagram illustratively shows workflow of the coordination module 22 during an image-guided biopsy procedure in accordance with one illustrative embodiment. In block 102, a decision is made as to whether the biopsy procedure has ended. In a first instance, the coordination module 22 starts with block 102. If the procedure is complete, the program path is terminated in block 112. If the procedure has not been completed, the path goes to block 104. In block 104, biopsy guidance with needle deployment detection is performed. This may include performing a biopsy procedure while monitoring a scanning device probe, such as, e.g., a transrectal ultrasonic (TRUS) probe, and/or monitoring a biopsy needle location. In block 106, sensors and/or algorithmic output is/are continuously monitored to determine a signal occurrence of a biopsy needle deployment. In block 108, if deployment is detected, the probe and/or biopsy needle locations are recorded, along with time of deployment in block 110. Deployment monitoring continues until the end of the biopsy procedure in block 112. The coordination module 22 may provide other methods for needle deployment as well. Examples of such methods are described as follows.

Figure 3:
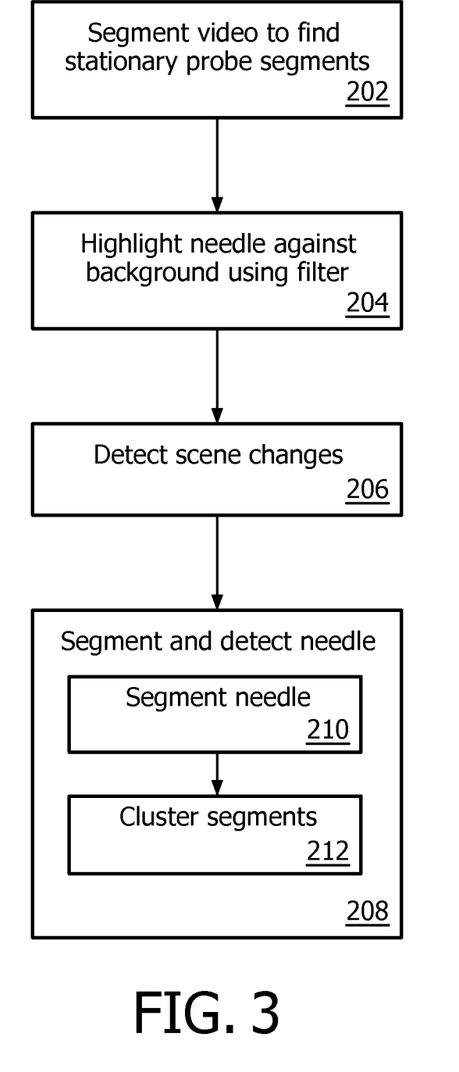
FIG. 3 is a block/flow diagram showing a system/method deployment detection using real-time images in accordance with the present principles.

Referring to FIG. 3, image based needle deployment detection detects biopsy needle deployment by integrating multi-source information of, e.g., ultrasound probe stability, a TRUS video background model, and prior knowledge of needle orientation and position. In block 202, EM-tracking information from the ultrasound probe sensor is employed to segment video into sections in which the ultrasound probe appears stationary. In block 204, the needle is highlighted using a filter specifically designed to respond to the biopsy needle inside an image. In block 206, scene changes are detected with respect to a background model that is maintained throughout each video segment. By combining these steps together, the presence of the biopsy needle can be detected in block 208. Further detail of each step is presented as follows.

In block 202, TRUS video partitions are based on probe stability. An observation about needle deployment is that urologists first stabilize the ultrasound probe and then they deploy the needle to get a sample, e.g., from a prostate or other organ or tissue. Under this observation, the search for the needle deployment is narrowed to the parts of the video sequence where the ultrasound probe is stationary.

Figure 4:
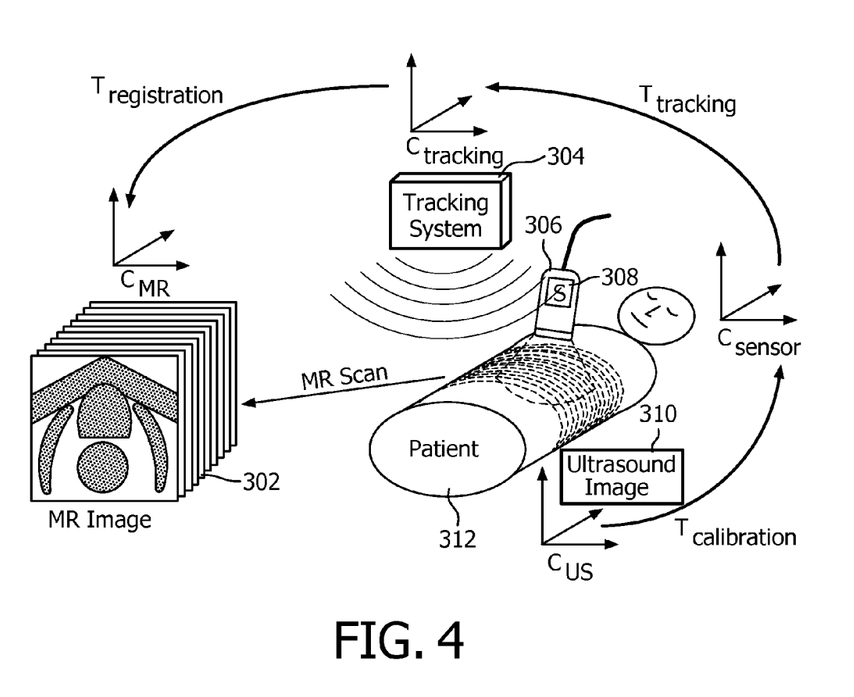
FIG. 4 is a diagram showing a transformation of real-time ultrasound images and tracking data to a reference image in accordance with one embodiment.

Referring to FIG. 4, a transformation chain for fusing a real-time TRUS image 310 and a pre-acquired MR image 302 is illustratively shown. The ultrasonic image 310 taken of a patient 312 includes a coordinate system $C_{US}$. A tracking sensor 308 which is attached to the ultrasound probe 306 has its own coordinate system $C_{sensor}$. A tracking system 304 includes its own coordinate system $C_{tracking}$. The MRI image 302 taken from an MR scan of the patient 312 includes its own coordinate system $C_{MR}$. These coordinate systems may be transformed to a reference coordinate system (e.g., $C_{MR}$) using transformations. These transformations include, e.g., $T_{calibration}$, $T_{tracking}$ and $T_{registration}$. With these transformations, three-dimensional (3D) world locations of the pixels can be found in a 2D TRUS frame (310). By comparing the 3D coordinates of the same set of pixels in consecutive frames, we can determine the motion of the US probe 306. In the present approach, N points are selected on the image plane (310). Then, the world coordinates of these points are found through EM-tracking of the probe 306. For each point, we compute an angular distance between the 3D world position of that point and its 3D world position at the previous frame. If none of these N points move significantly, we tag the frame as "stationary" and the frame thus is a candidate for further processing.

Figure 5:
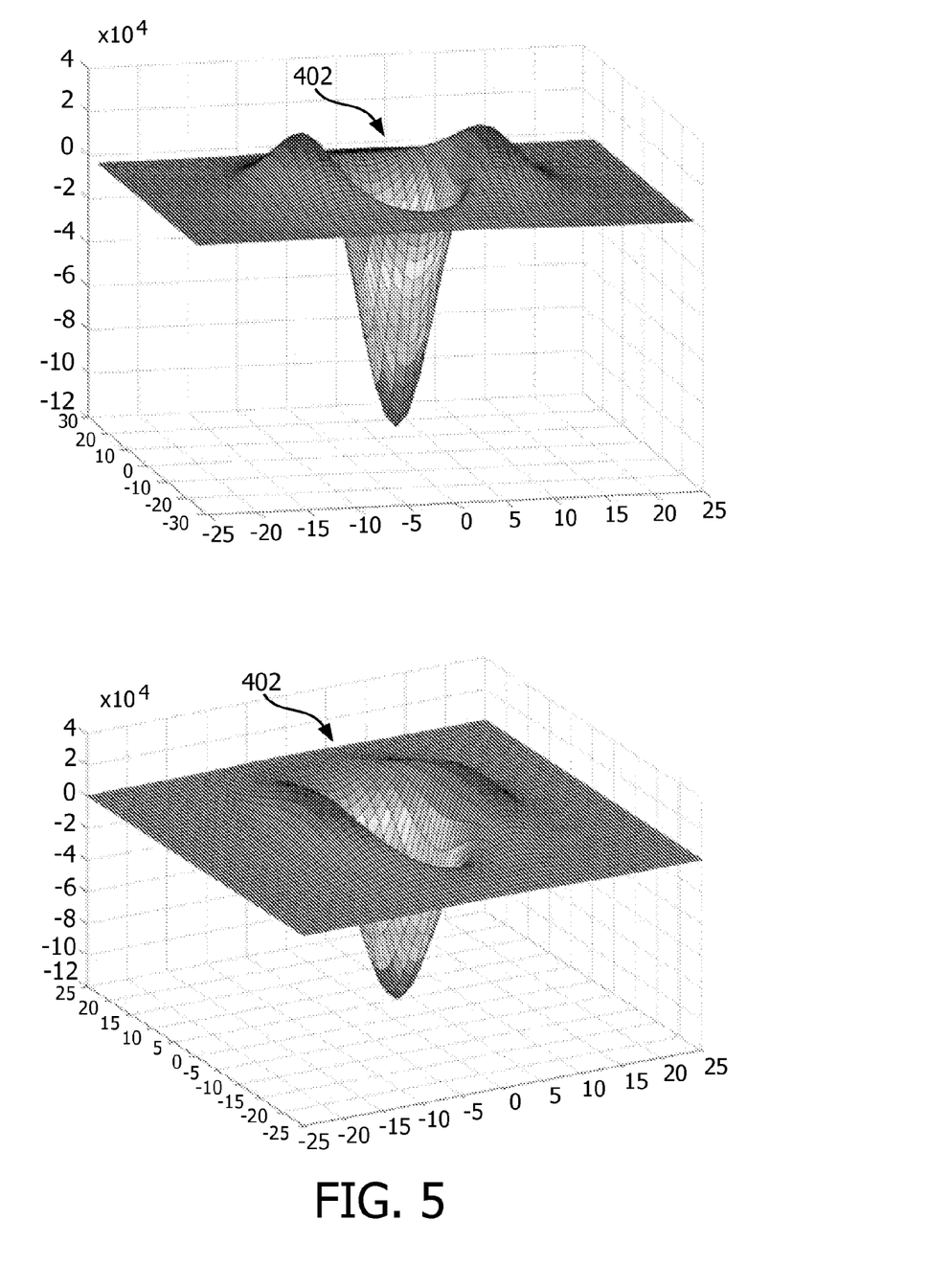
FIG. 5 shows diagrams of an illustrative filter employed to highlight a biopsy needle in an image in accordance with one embodiment.

Referring again to FIG. 3, in block 204, the needle is highlighted. Once the TRUS frames (310) captured when the US probe position is stable are identified, the needle is detected and segmented in those frames, if possible. The image may be convolved first with a filter before processing. A specific design for the filter can aid in exploiting the tubular structure of the needle instead of just suppressing noise in the image. In one embodiment, a $2^{nd}$ derivative Gaussian filter may be employed. FIG. 5 shows two illustrative perspective views of a $2^{nd}$ derivative Gaussian filter 402. The $2^{nd}$ derivative Gaussian filter 402 exploits the cylindrical shape of the needle to assist in enhancing the needle in an ultrasonic image.

In block 206, background modeling for change detection is performed. After filtering the US images using the needle detection filter, needle deployment is detected by finding a sudden frame appearance change. When the ultrasound probe is stable, the only change happening in the scene is deployment of the needle as the respiratory motion can be ignored. To detect this significant change, a histogram of the filter response may be employed which is also invariant under small respiratory motion.

In block 208, needle segmentation is performed. The change detection described in block 206 may not only mark the frames with needle deployment but also may mark false-positive frames where there is no needle appearance. To eliminate the false positives, the needle may be segmented inside the image to verify its presence. In block 210, the image is segmented into needle pieces and background using the filter response. Graph-cuts for segmentation may be used, however, more than one segment may be output as the needle. In block 212, these segments are clustered based on prior knowledge of the position and orientation of a needle guide. Clustering of the pieces that form a tubular structure is favored. Graph-cuts may also be employed for this purpose.

Once the segmentation of the needle is obtained, many false positives can be eliminated based on the shape, orientation and position with respect to the needle guide. This approach helps to reliably eliminate the vast majority of frames without needle deployments. The fired needle can then be detected.

Note that needle location detection in accordance with FIG. 3 uses spatial tracking of the ultrasound probe or biopsy guide, which are used for the biopsy procedure. Spatial tracking of the biopsy needle itself (using an additional tracking sensor) is not needed. However, if this method is used as the only way of deployment detection, the recording of the exact biopsy needle tip or biopsy core location (i.e., the depth of needle insertion along the needle path) may not be available.

Figure 6:
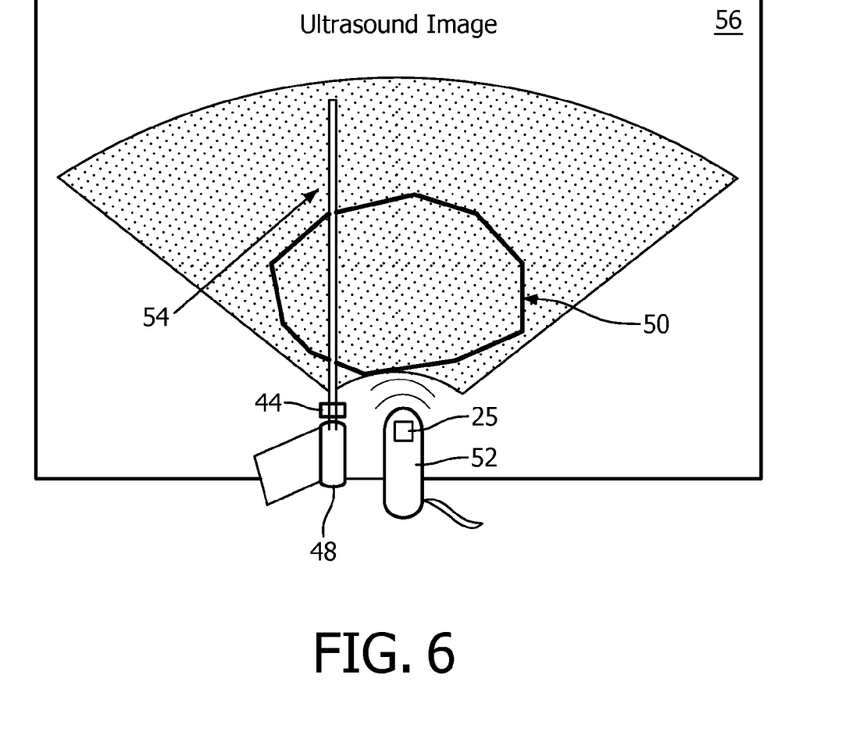
FIG. 6 is an illustrative ultrasonic image showing motion based needle deployment detection in accordance with another embodiment.

Referring to FIG. 6, in another embodiment, motion based needle deployment detection is provided. When a biopsy gun 48 is fired, an ultrasound probe 52 used to guide a needle 54 experiences some motion and vibration. This method of deployment detection in, e.g., an ultrasound image 56 exploits this vibration and sudden motion by attaching a vibration/motion detector 44 to the biopsy gun 48, and continuously monitoring a signal from the vibration/motion sensor 44. This method is simple and easy to use, and permits recording of needle deployment times. In combination with spatial tracking (25) of the TRUS probe 52 (or needle guide), this method also permits recording the location of the biopsy needle deployment path, e.g., in an organ 50, at the time of biopsy. The method of deployment detection in accordance with FIG. 6 may not permit recording of the exact biopsy needle tip or biopsy core location (i.e., the depth of needle insertion along the needle path).

In other embodiments, combined detection methods may be employed. For example, the combined methods may include using vibrations, acoustics and images together, or may include other combinations. The described embodiments can be combined together in different ways to achieve robust and reliable needle deployment detection. This can improve the detection performance over using any single method or technique. Coordinating multiple methods may also permit more accurate tracking and recording of the number and time of deployments, and also actual biopsy needle locations.

In another embodiment, deployment detection with spatial tracking of a biopsy needle is employed. The spatial tracking described may be provided as an independent method or may be employed in combination with any other described methods.

Figure 7:
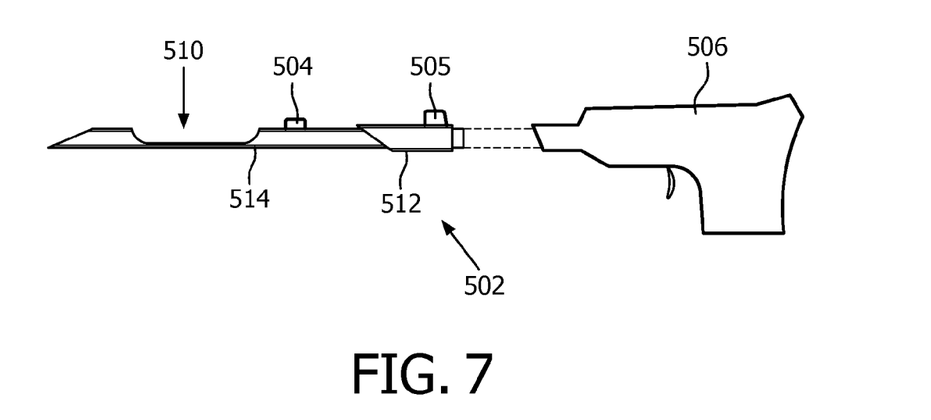
FIG. 7 is a diagram showing a biopsy gun and needle having a stationary tracking device and a moving tracking device on the needle in accordance with another embodiment.

Referring to FIG. 7, a needle deployment can be automatically detected, and a location of a biopsy core 510 can be determined by spatial tracking of a biopsy needle 502. For that purpose, a tracking sensor or sensors 504 or 505 are provided on a biopsy gun 506 and can be attached either on a "stationary" (505) or on a "moving" (504) reference point of the biopsy needle 502. A stationary reference point does not move relative to a needle shaft when the biopsy gun 506 is fired. The stationary reference point may be located on an outer core 512 of the needle 502. A moving reference point moves forward along a needle axis with a needle deployment mechanism when the biopsy gun 506 is fired. The moving reference point may be located on an inner stylet 514 of the needle 502.

Tracking sensors 505 on a stationary reference point are easier/cheaper to manufacture, but the spatial position tracking from the "stationary" sensor 505 does not directly reflect the motion of the needle tip during deployment. Thus, for deployment detection, this sensor 505 is preferably employed in combination with the methods described, e.g., in FIGS. 3, 4, 5, 6, etc. In particular, the signal from the tracking sensor 504 can be used to act as the vibration/motion sensor (44). Tracking sensors 504 on a "moving" point of the needle 502 can be used directly to detect the deployment of the needle 502 (sensor 504 will quickly move a fixed distance along the needle axis), and to record its location.

Figure 8:
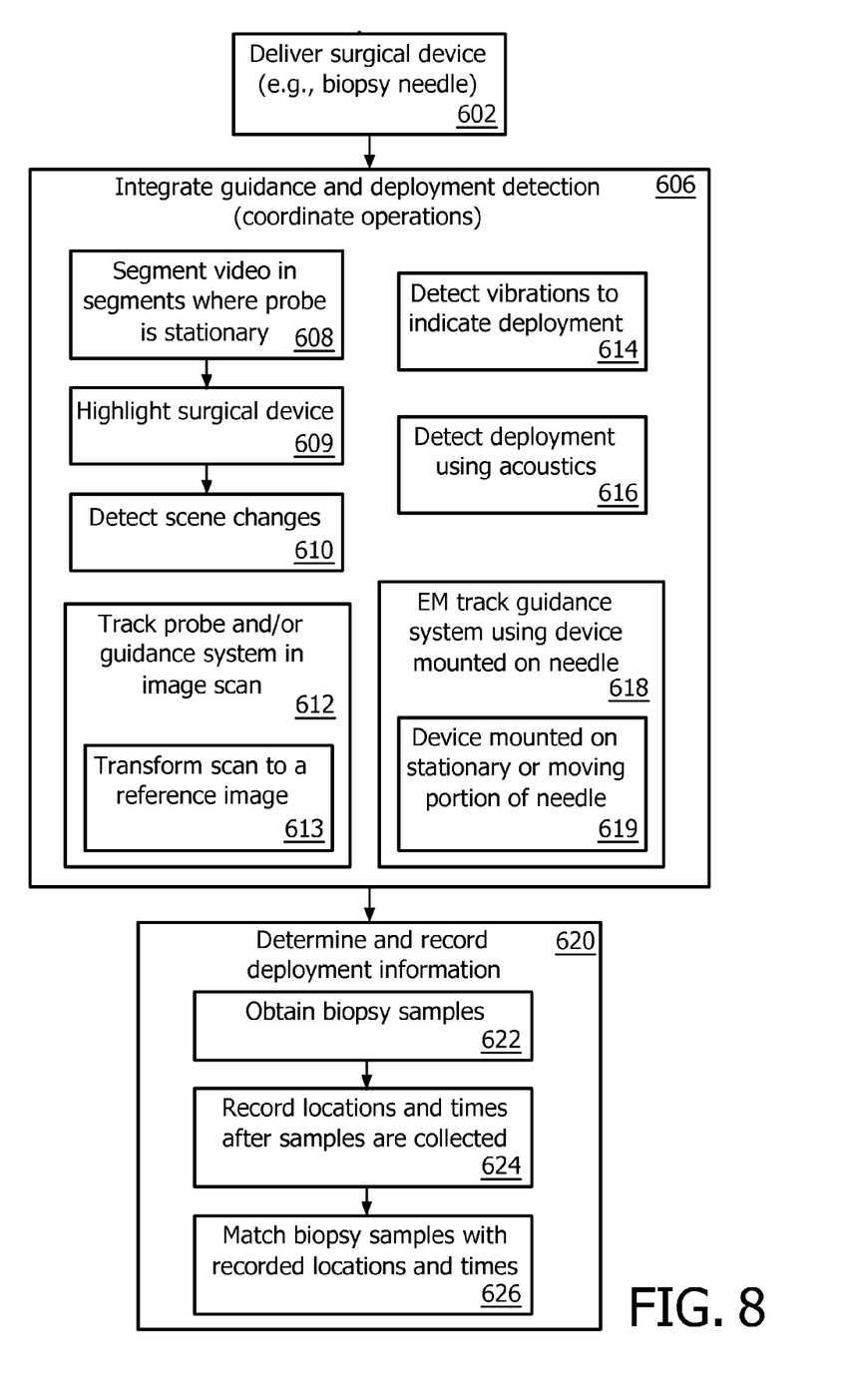
FIG. 8 is a flow diagram showing a method for surgical instrument guidance and deployment detection in accordance with the present principles.

Referring to FIG. 8, a method for medical device detection is described in accordance with one embodiment. In block 602, a surgical device is delivered into a subject using a guidance system. The surgical device may include a biopsy needle.

In block 606, surgical device guidance is integrated with automatic deployment detection and recordation to detect an occurrence of a deployment of the surgical device with one or more of a real-time image, an acoustic indicator, a vibration detector and a spatial tracking device. Deployment may mean an insertion of the device into a subject or, more preferably, a triggering of the device to collect a biopsy sample or the like. It is preferable that the detected event be the triggering event to take a biopsy sample so that a position and time of the biopsy sample is more precisely determined by the system.

Detecting deployment of the surgical device with a real-time image may include segmenting video into sections in which an ultrasound probe is stationary in block 608; highlighting the surgical device in the sections of video using a filter in block 609; and detecting scene changes with respect to a background model that is maintained throughout video segments to determine a presence of a biopsy needle in block 610.

In block 612, the real-time image is ultrasonically scanned such that at least one of an ultrasonic scan probe and the guidance system has a position tracked by a tracking system. The real-time image may be transformed into a reference medical image in block 613.

In block 614, detecting deployment of the surgical device with a vibration detector includes detecting vibrations in the surgical device to indicate the deployment. In block 616, detecting deployment of the surgical device with an acoustic indicator includes acoustically indicating a position of the guidance system (e.g., audio sound increases with needle depth or upon firing needle).

In block 618, detecting deployment of the surgical device with a spatial tracking device includes electromagnetically tracking a position of the guidance system using a spatial tracking device mounted on a biopsy needle. In block 619, tracking a position of the guidance system using a spatial tracking device mounted on a biopsy needle includes one of a stationary and a moving spatial tracking device. It should be understood that one or more of the detection methods of block 606 may be employed together in combination.

In block 620, one or more of a location and time of each deployment is determined and recorded based upon the surgical device guidance and automatic deployment detection. In block 622, determining and recording includes obtaining biopsy samples and recording a number of biopsies and a location and time of each biopsy. In block 624, the guidance system and the automatic deployment detection are coordinated to record a number of deployments, locations of each deployment and time of each deployment after a deployment is detected. In block 626, the biopsy samples may be matched (references) to the locations and times recorded.

In interpreting the appended claims, it should be understood that:
   a) the word "comprising" does not exclude the presence of other elements or acts than those listed in a given claim;
   b) the word "a" or "an" preceding an element does not exclude the presence of a plurality of such elements;
   c) any reference signs in the claims do not limit their scope;
   d) several "means" may be represented by the same item or hardware or software implemented structure or function; and
   e) no specific sequence of acts is intended to be required unless specifically indicated.

Having described preferred embodiments for systems and methods for needle deployment detection in image-guided biopsies (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for medical device detection, comprising:
   a guidance system configured to deliver a surgical device into a subject;
   a surgical device deployment detector configured to cooperate with the guidance system and configured to detect a deployment of the surgical device in the subject; and
   a coordination module configured to receive feedback concerning delivery of the surgical device from the guidance system and the deployment detector to coordinate a plurality of inputs to correlate a location of a detection of the surgical device with respect to a reference coordinate system; and based on the correlation, to determine and record the location, and a time of each deployment, wherein the correlation results from a coordinate system transformation chain, which fuses a real-time image and a pre-acquired image.

2. The system as recited in claim 1, further comprising a filter configured to highlight the surgical device in an ultrasonic image scan.

3. The system as recited in claim 1, wherein the surgical device deployment detector includes a vibration detector mounted on the guidance system wherein said vibration detector is configured to detect a deployment of the surgical device.

4. The system as recited in claim 1, wherein the surgical device deployment detector includes an acoustic detector configured to acoustically indicate a position of the guidance system.

5. The system as recited in claim 1, wherein the surgical device deployment detector includes a spatial tracking system, wherein the spatial tracking system includes a spatial tracking device mounted on a biopsy needle which includes one of a stationary and a moving spatial tracking device.

6. The system as recited in claim 1, wherein the coordinate system transformation chain comprises a transformation of a plurality of real-time image coordinate systems to a pre-acquired image coordinate system.

7. The system in claim 1, wherein, based on the transformation chain real-time locations of pixels in three-dimensions can be presented in a real-time two-dimensional frame.

8. A biopsy system for medical device detection, comprising:
   a guidance system configured to deliver a biopsy needle into a subject;
   a deployment detector configured to detect deployment of the biopsy needle and a scanning probe employed to image the biopsy needle;
   an imaging device configured to image the deployment; and
   a coordination module configured to receive feedback concerning delivery of a surgical device from the guidance system, the deployment detector and the scanning probe to coordinate a plurality of inputs to record each deployment to correlate a location of detection of the surgical device with respect to a reference coordinate system; and based on the correlation, to create a record of the location and a time of a biopsy associated with each deployment, wherein the correlation results from a coordinate system transformation chain which fuses a real-time image and a pre-acquired image.

9. The system as recited in claim 8, further comprising a filter configured to highlight the biopsy needle in an ultrasonic image scan.

10. The system as recited in claim 8, wherein the deployment detector includes a vibration detector mounted on the guidance system wherein said vibration detector is configured to detect a deployment of the surgical device.

11. The system as recited in claim 8, wherein the deployment detector includes an acoustic detector configured to acoustically indicate a position of the guidance system.

12. The system as recited in claim 8, wherein the deployment detector includes a spatial tracking system, wherein the spatial tracking system includes a spatial tracking device mounted on the biopsy needle which includes one of a stationary and a moving spatial tracking device.

13. A method for medical device detection, comprising:
   delivering a surgical device into a subject using a guidance system;
   integrating surgical device guidance with automatic deployment detection and recordation to detect an occurrence of a deployment of the surgical device with one or more of a real-time image, an acoustic indicator, a vibration detector and a spatial tracking device;
   coordinating a plurality of inputs including feedback concerning the delivering of the surgical device from the surgical device guidance and automatic deployment detection;
   effecting a coordinate system transformation chain, which fuses a real-time image and a pre-acquired image, to correlate a location of a detection of the surgical device with respect to a reference coordinate system; and
   based on the correlation, determining and recording of the location and a time of each deployment in the reference coordinate system.

14. The method as recited in claim 13, wherein deployment detection of the surgical device with a vibration detector includes detecting vibrations in the surgical device to indicate the deployment.

15. The method as recited in claim 13, wherein deployment detection of the surgical device with an acoustic indicator includes acoustically indicating a position of the guidance system.

16. The method as recited in claim 13, wherein deployment detection of the surgical device with a spatial tracking device includes electromagnetically tracking a position of the guidance system using a spatial tracking device mounted on a biopsy needle, the spatial tracking device including one of a stationary and a moving spatial tracking device.

17. The method as recited in claim 13, wherein detecting deployment of the surgical device with a real-time image includes:
   segmenting video into sections in which an ultrasound probe is stationary;
   highlighting the surgical device in the sections of video using a filter; and
   detecting scene changes with respect to a background model that is maintained throughout video segments to determine a presence of a biopsy needle.

18. The method as recited in claim 13, wherein the acoustic indicator and/or the vibration detector are solely used for the step of integrating surgical device guidance with automatic deployment detection and recordation.

19. The system as recited in claim 13, wherein the coordinate system transformation chain comprises a transformation of a plurality of real-time image coordinate systems to a pre-acquired image coordinate system.

20. The system in claim 13, wherein, based on the transformation chain real-time locations of pixels in three-dimensions can be presented in a real-time two-dimensional frame.

21. The method as recited in claim 13, wherein the effecting the coordinate system transformation chain comprises transforming a plurality of real-time image coordinate systems to a pre-acquired image coordinate system.

* * * * *